US00PP21010P2

(12) United States Plant Patent
Dresselhuys

(10) Patent No.: US PP21,010 P2
(45) Date of Patent: May 25, 2010

(54) ***CHRYSANTHEMUM* PLANT NAMED 'FANCY YOURSULA'**

(50) Latin Name: *Chrysanthemum×morifolium*
Varietal Denomination: Fancy Yoursula

(75) Inventor: Henk Dresselhuys, De Lier (NL)

(73) Assignee: Yoder Brother, Inc., Barberton, OH (US)

( * ) Notice: Subject to any disclaimer, the term of this patent is extended or adjusted under 35 U.S.C. 154(b) by 0 days.

(21) Appl. No.: 12/319,415

(22) Filed: Jan. 7, 2009

(51) Int. Cl.
*A01H 5/00* (2006.01)

(52) U.S. Cl. ..... Plt./290

(58) Field of Classification Search ..... Plt./290, Plt./287

See application file for complete search history.

*Primary Examiner*—June Hwu
(74) *Attorney, Agent, or Firm*—C. A. Whealy

(57) ABSTRACT

A new and distinct cultivar of *Chrysanthemum* plant named 'Fancy Yoursula', characterized by its compact, upright, outwardly spreading and mounded plant habit; very freely branching habit; dense and full plant habit; uniform and freely flowering habit; small decorative-type inflorescences with ligulate-shaped ray florets; orange bronze-colored ray florets; and natural season flowering date of about September 14$^{th}$ in the Northern Hemisphere.

1 Drawing Sheet

Botanical designation: *Chrysanthemum×morifolium.*
Cultivar denomination: 'Fancy Yoursula'.

BACKGROUND OF THE INVENTION

The present invention relates to a new and distinct cultivar of *Chrysanthemum* plant, botanically known as *Chrysanthemum×morifolium*, commercially grown as a perennial garden *Chrysanthemum* plant, and hereinafter referred to by the name 'Fancy Yoursula'.

The new *Chrysanthemum* plant is a naturally-occurring whole plant mutation of *Chrysanthemum×morifolium* 'Festive Yoursula', disclosed in U.S. Plant Pat. No. 15,324. The new *Chrysanthemum* plant was discovered and selected by the Inventor as a single flowering plant from within a population of plants of 'Yoursula' in a controlled greenhouse environment in De Lier, The Netherlands in September, 2006.

Asexual reproduction of the new *Chrysanthemum* plant by vegetative cuttings was first conducted in a controlled greenhouse environment in De Lier, The Netherlands in November, 2006. Asexual reproduction by cuttings has shown that the unique features of this new *Chrysanthemum* plant are stable and reproduced true to type in successive generations.

SUMMARY OF THE INVENTION

Plants of the new *Chrysanthemum* have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Fancy Yoursula'. These characteristics in combination distinguish 'Fancy Yoursula' as a new and distinct garden *Chrysanthemum* cultivar:

1. Compact, upright, outwardly spreading and mounded plant habit.
2. Very freely branching habit; dense and full plant habit.
3. Uniform and freely flowering habit.

4. Small decorative-type inflorescences with ligulate-shaped ray florets.
5. Orange bronze-colored ray florets.
6. Natural season flowering occurs about September 14$^{th}$ in the Northern Hemisphere.

In side-by-side comparisons conducted in Alva, Fla., plants of the new *Chrysanthemum* differed from plants of the parent, 'Festive Yoursula', in the following characteristics:

1. Plants of the new *Chrysanthemum* were more compact than plants of 'Festive Yoursula'.
2. Plants of the new *Chrysanthemum* and 'Festive Yoursula' differed in ray floret color as plants of 'Festive Yoursula' had bronze-colored ray florets.
3. Ray floret color of plants of the new *Chrysanthemum* was longer lasting than ray floret color of plants of 'Festive Yoursula'.

Plants of the new *Chrysanthemum* can be compared to plants of *Chrysanthemum×morifolium* 'Warm Yoursula', disclosed in U.S. Plant Pat. No. 16,146. In side-by-side comparisons conducted in Alva, Fla., plants of the new *Chrysanthemum* differed from plants of 'Warm Yoursula' in the following characteristics:

1. Plants of the new *Chrysanthemum* were more compact than plants of 'Warm Yoursula'.
2. Plants of the new *Chrysanthemum* flowered earlier than plants of 'Warm Yoursula' when grown under natural season conditions.
3. Ray floret color of plants of the new *Chrysanthemum* was longer lasting than ray floret color of plants of 'Warm Yoursula'.

Plants of the new *Chrysanthemum* can be compared to plants of *Chrysanthemum×morifolium* 'Katelli', disclosed in U.S. Plant Pat. No. 16,674. In side-by-side comparisons conducted in Alva, Fla., plants of the new *Chrysanthemum* differed from plants of 'Katelli' in the following characteristics:

1. Plants of the new *Chrysanthemum* were more compact and more spherical in shape than plants of 'Katelli'.

2. Plants of the new *Chrysanthemum* flowered three days earlier than plants of 'Katelli' when grown under natural season conditions.
3. Ray floret color of plants of the new *Chrysanthemum* was lighter than ray floret color of plants of 'Katelli'.

BRIEF DESCRIPTION OF THE PHOTOGRAPHS

The accompanying photographs illustrate the overall appearance of the new *Chrysanthemum*. These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the bottom of the sheet comprises a side perspective view of a typical flowering plant of 'Fancy Yoursula' grown in a container.

The photograph at the top of the sheet is a close-up view of typical inflorescences of 'Fancy Yoursula'.

DETAILED BOTANICAL DESCRIPTION

The aforementioned photographs and following observations and measurements describe plants grown in Alva, Fla. during the autumn in a polycarbonate-covered greenhouse and under conditions and practices which approximate those generally used in commercial garden *Chrysanthemum* production. During the production of the plants, day temperatures averaged 29° C. and night temperatures averaged 18° C. Plants were grown in 10-cm containers under short day/long night conditions. Plants were pinched one time about two weeks after planting and had been growing for eight weeks when the photographs and description were taken. In the following description, color references are made to The Royal Horticultural Society Colour Chart, 2007 Edition, except where general terms of ordinary dictionary significance are used.

Botanical classification: *Chrysanthemum×morifolium* 'Fancy Yoursula'.

Parentage:

Naturally-occurring whole plant mutation of *Chrysanthemum×morifolium* 'Festive Yoursula', disclosed in U.S. Plant Pat. No. 15,324.

Propagation:

*Type.*—Terminal vegetative cuttings.

*Time to initiate roots.*—About four days at temperatures of about 21° C.

*Time to produce a rooted young plant.*—About ten to twelve days at temperatures of about 21° C.

*Root description.*—Fine, fibrous; white in color.

*Rooting habit.*—Freely branching.

Plant description:

*Appearance.*—Perennial decorative-type garden *Chrysanthemum*; compact plant habit with stems upright and outwardly spreading giving a uniformly mounded appearance to the plant; very freely branching habit, about nine to ten lateral branches each with multiple secondary branches; pinching enhances lateral branch development; dense and full plant habit; strong and vigorous growth habit.

*Plant height.*—About 19 cm.

*Plant width.*—About 26 cm.

*Lateral branches.*—Length: About 17 cm. Diameter: About 4.5 mm. Internode length: About 1.8 cm. Strength: Strong. Texture: Pubescent; longitudinally ridged. Color: Close to 138A.

*Leaves.*—Arrangement: Alternate, simple. Length: About 4.8 cm. Width: About 4.4 cm. Apex: Mucronate. Base: Attenuate. Margin: Palmately lobed, sinuses between lateral lobes nearly parallel. Texture, upper and lower surfaces: Pubescence; veins prominent on lower surface. Color: Developing and fully expanded leaves, upper surface: Close to N137A; venation, close to N137B. Developing and fully expanded leaves, lower surface: Close to 147B; venation, close to 147B. Petiole: Length: About 1.8 cm. Diameter: About 3 mm. Texture, upper and lower surfaces: Pubescent. Color, upper surface: Close to 137B. Color, lower surface: Close to 137C.

Inflorescence description:

*Appearance.*—Decorative-type inflorescence form with ligulate-shaped ray florets; inflorescences borne on terminals above foliage; disc and ray florets arranged acropetally on a capitulum.

*Fragrance.*—Faintly fragrant, pungent.

*Flowering response.*—Under natural season conditions, plants flower about September 14$^{th}$ in the Northern Hemisphere.

*Postproduction longevity.*—Inflorescences maintain good color and substance for about 4.5 weeks in an outdoor nursery; inflorescences persistent.

*Quantity of inflorescences.*—About 13 inflorescences develop per lateral branch.

*Inflorescence bud.*—Height: About 1.3 cm. Diameter: About 1.2 cm. Shape: Oblate. Color: Close to 165B.

*Inflorescence size.*—Diameter: About 4.5 cm. Depth (height): About 1.8 cm. Disc diameter: About 5 mm. Receptacle diameter: About 1.8 cm. Receptacle height: About 5 mm. Receptacle color: Close to 137A.

*Ray florets.*—Shape: Ligulate. Orientation: Initially upright, then perpendicular to peduncle with apices reflexing with development. Aspect: Initially incurved, then mostly flat. Length: About 2.1 cm. Width: About 7 mm. Apex: Shallowly emarginate. Base: Attenuate. Margin: Entire. Texture, upper and lower surfaces: Smooth, glabrous; longitudinally ribbed. Number of ray florets per inflorescence: About 158 arranged in about twelve whorls. Color: When opening, upper surface: Close to 167A to 167B. When opening, lower surface: Close to 163C. Fully opened, upper surface: Close to 166D; color becoming closer to N167C with development. Fully opened, lower surface: Close to 163C tinted with close to 164B; color does not fade with development.

*Disc florets.*—Shape: Tubular, elongated. Length: About 5 mm. Diameter: About 2 mm. Number of disc florets per inflorescence: About 35. Color, immature: Apex: Close to 1A. Mid-section: Close to 11A. Base: Close to 157D. Color, mature: Apex: Close to 6C. Mid-section: Close to 11A. Base: Close to 157D.

*Phyllaries.*—Number of phyllaries per inflorescence: About 20 arranged in about three whorls. Length: About 7 mm. Width: About 2.5 mm to 3 mm. Shape: Elliptical. Apex: Acute. Base: Truncate. Margin: Entire. Texture, upper surface: Smooth, glabrous. Texture, lower surface: Pubescent. Color, upper surface: Close to 146A. Color, lower surface: Close to N137B.

*Peduncles.*—Length, terminal peduncle: About 4.2 cm. Length, fourth peduncle: About 6.8 cm. Diameter, terminal peduncle: About 2.5 mm. Angle: Mostly upright to 35° to 45° from vertical. Strength: Strong. Texture: Pubescent. Color: Close to 146B.

*Reproductive organs.*—Androecium (Present on disc florets only): Stamen number: About five per floret. Filament length: About 2.5 mm. Filament color: Close to 157D. Anther length: About 1.5 mm. Anther shape: Oblong. Anther color: Close to 11B. Pollen amount: Scarce. Pollen color: Close to 11B. Gynoecium (Present on both ray and disc florets): Pistil length: About 6 mm. Stigma shape: Bi-parted. Stigma color: Close to 3A. Style length: About 3 mm. Style color: Close to 1C. Ovary color: Close to NN155D.

*Seed/fruit.*—Seed and fruit production have not been observed.

Disease/pest resistance: Resistance to pathogens and pests common to *Chrysanthemums* has not been observed on plants grown under commercial conditions.

Garden performance: Plants of the new *Chrysanthemum* have demonstrated excellent garden performance and will tolerate temperatures ranging from about 0° C. to about 38° C.

It is claimed:

1. A new and distinct *Chrysanthemum* plant named 'Fancy Yoursula' as illustrated and described.

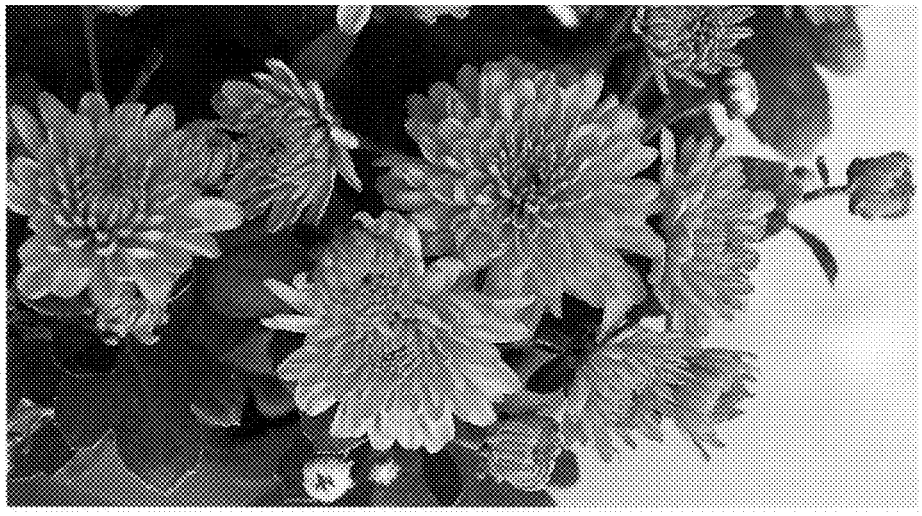
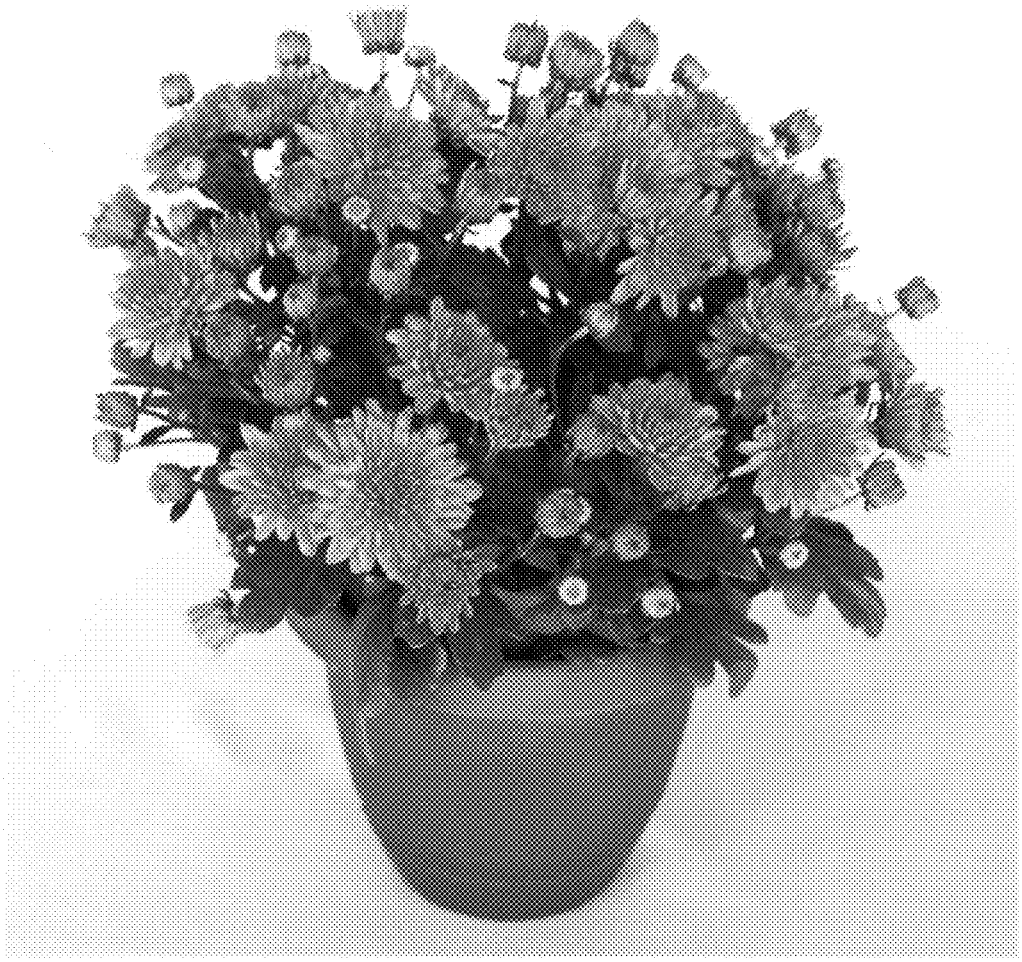

* * * * *